(12) United States Patent
Greene et al.

(10) Patent No.: US 10,247,667 B2
(45) Date of Patent: Apr. 2, 2019

(54) PHOTON MARKER SYSTEM FOR FIBER MATERIAL

(71) Applicant: Fibremark Solutions Limited, Eastbourne, East Sussex (GB)

(72) Inventors: Morton Greene, Las Vegas, NV (US); Paul Stenning, Eastbourne (GB)

(73) Assignee: FIBREMARK SOLUTIONS LIMITED, Eastbourne, East Sussex (GB)

( * ) Notice: Subject to any disclaimer, the term of this patent is extended or adjusted under 35 U.S.C. 154(b) by 0 days.

(21) Appl. No.: 15/961,184

(22) Filed: Apr. 24, 2018

(65) Prior Publication Data

US 2018/0313750 A1 Nov. 1, 2018

Related U.S. Application Data

(60) Provisional application No. 62/602,514, filed on Apr. 26, 2017.

(51) Int. Cl.
*G01N 21/35* (2014.01)
*G01N 21/95* (2006.01)
(Continued)

(52) U.S. Cl.
CPC ......... *G01N 21/3563* (2013.01); *A41D 31/00* (2013.01); *C09K 11/02* (2013.01); *C09K 11/025* (2013.01); *C09K 11/08* (2013.01); *D01F 1/04* (2013.01); *D01F 2/00* (2013.01); *D02G 3/346* (2013.01); *G01N 21/3581* (2013.01);
(Continued)

(58) Field of Classification Search
CPC ......... C09K 11/025; C09K 11/08; D01F 1/04; D03D 15/0022; D03D 2700/0174; D03D 2700/0192; D04B 1/16; D04B 21/16; D10B 2201/02; D10B 2401/20; D10B 2501/00; G01N 21/3563; G01N 21/3581; G01N 21/952
See application file for complete search history.

(56) References Cited

U.S. PATENT DOCUMENTS 4,527,383 A 7/1985 Bingham
5,770,110 A 6/1998 Schrell
(Continued)

FOREIGN PATENT DOCUMENTS

CN 101298705 A 11/2008
DE 10 2005 047 786 A1 4/2007
WO 2011/098083 A1 8/2011

*Primary Examiner* — Mark R Gaworecki
(74) *Attorney, Agent, or Firm* — Seth Natter; Natter & Natter

(57) ABSTRACT

Rare earth ceramic pigment luminescent nano-particle photon markers are mixed in specific proportions within cellulose slurry and extruded to form trace fiber strands. The trace fiber strands are processed into slivers and are blended with a base fiber or fibers at specific concentration levels. The number and proportion of different photon markers and their concentration levels within the yarn, thread, cloth, fabric, textile or garment generate specific photonic response signatures when examined under a spectrophotometer reader. Signatures may be assigned representing provenance, base fiber identification, base fiber concentration, the manufacturer, and/or other data throughout the manufacturing and supply chain of a finished product.

16 Claims, 7 Drawing Sheets

(51) Int. Cl.
*D01F 1/04* (2006.01)
*C09K 11/08* (2006.01)
*C09K 11/02* (2006.01)
*A41D 31/00* (2019.01)
*G01N 21/64* (2006.01)
*G01N 21/3563* (2014.01)
*G01N 21/3581* (2014.01)
*G01N 21/952* (2006.01)
*D02G 3/34* (2006.01)
*D01F 2/00* (2006.01)
*D04B 1/16* (2006.01)
*D04B 21/16* (2006.01)
*D03D 15/00* (2006.01)

(52) U.S. Cl.
CPC ....... *G01N 21/6428* (2013.01); *G01N 21/952* (2013.01); *D03D 15/0022* (2013.01); *D03D 2700/0174* (2013.01); *D03D 2700/0192* (2013.01); *D04B 1/16* (2013.01); *D04B 21/16* (2013.01); *D10B 2201/02* (2013.01); *D10B 2401/20* (2013.01); *D10B 2501/00* (2013.01)

(56) References Cited

U.S. PATENT DOCUMENTS

| | | | |
|---|---|---|---|
| 6,515,113 | B2 | 2/2003 | Raymond |
| 9,234,131 | B2 | 1/2016 | Imbert |
| 9,718,298 | B2 | 8/2017 | Quintela |
| 2003/0089782 | A1* | 5/2003 | Reed ........................ D06H 1/00 235/468 |
| 2008/0293052 | A1* | 11/2008 | Liang ..................... C09D 11/03 435/6.11 |
| 2008/0299559 | A1* | 12/2008 | Kwok .................... C09D 11/03 435/6.12 |
| 2014/0103226 | A1* | 4/2014 | Lopez Quintela ..... B41M 3/144 250/459.1 |
| 2015/0177423 | A1 | 6/2015 | Scipioni |
| 2015/0377841 | A1* | 12/2015 | Gaynor .................... A24D 3/04 436/154 |
| 2015/0377854 | A1* | 12/2015 | Gaynor .................... A24D 3/00 73/23.37 |
| 2016/0140427 | A1* | 5/2016 | Keay ...................... G07D 7/121 235/494 |

* cited by examiner

PHOTON MARKER SYSTEM FOR FIBER MATERIAL

RELATED APPLICATIONS

This application claims the priority benefit of Application No. 62/602,514 filed Apr. 26, 2017, the entirety of the contents of which are hereby incorporated herein by reference.

FIELD OF THE INVENTION

This invention relates generally to fiber materials employed in the manufacture of textiles, fabrics, garments, cloth, yarns, threads and the like and more specifically to a system employing trace fiber strands doped with photon markers for authentication and provenance from yarn or thread production through manufacture and distribution of finished products.

ANTECEDENTS OF THE INVENTION

Manufacturers of branded fashion clothing and accessories have been faced with a virtual flood of counterfeit products. Additionally, manufacturers must verify the source and authenticity of source materials, e.g. yarn and thread fibers, employed in the manufacturing process. Representations that a garment has been manufacture from US cotton or Egyptian cotton in their entirety or in certain percentages must be verified as well as other fiber content representations, e.g. synthetic fiber content, to assure that there has been no fiber adulteration.

Tens of thousands of shipments of counterfeit apparel and accessories with an estimated value in excess of one hundred million dollars have been seized in in the United States in one year alone. The extent and value of counterfeit apparel and accessories which have not been detained presents a serious challenge not only to manufacturers, but to the economy as a whole.

Various attempts have been made to verify the authenticity of garments. Disclosed in U.S. Pat. No. 4,527,383 was a system of producing a thread or yarn which carried a polymeric filament intertwined with other fibers. The polymeric filament comprised a slit fiber having a width of 0.135 to 0.37 mm bearing coded indicia for identification of the garment. Manual observation under magnification was required and the indicia would only indicate a single attribute of the fabric or garment.

There remained a need for a system of quickly and accurately ascertaining authenticity, purity and provenance of yarns, threads, cloth, fabrics, finished textiles, garments and the like which can be employed at any stage of manufacture and distribution.

SUMMARY OF THE INVENTION

Microcapsules comprising luminescent nano-particle photon markers encased in shells are mixed in specific proportions within a diluted cellulose slurry and the mixture is extruded through a spinneret to form trace fiber strands. The trace fiber strands are processed into slivers and are blended with a base fiber or fibers at specific concentration levels at either the ginning or yarn spinning stage.

The number and proportion of different photon marker microcapsules employed and their concentration levels within the yarn, thread, cloth, fabric textile or garment generate specific signatures when examined under a spectrophotometer reader. Signatures may be assigned representing fiber identification, fiber adulteration, the identity of the manufacturer of the finished product, the garment or product style number, the production season, etc.

From the foregoing compendium, it will be appreciated that a feature of the present invention is to provide a photon marker system for fiber material of the general character described which is not subject to the disadvantages of the aforementioned antecedents of the invention.

An aspect of the present invention is to provide a photon marker system for fiber material of the general character described which is capable of verifying multiple fiber characteristics.

A consideration of the present invention is to provide a photon marker system for fiber material of the general character described which is easy to use.

A further feature of the present invention is to provide a photon marker system for fiber material of the general character described which is relatively low in cost and well suited for economical mass production fabrication.

Another consideration of the present invention is to provide a photon marker system for fiber material of the general character described which efficiently detects fiber adulteration.

A further aspect of the present invention is to provide a photon marker system for fiber material of the general character described wherein trace fiber slivers carrying photon markers are blended with base fibers.

An additional feature of the present invention is to provide a photon marker system for fiber material of the general character described which may be employed at various stages of manufacture and distribution of finished product.

To provide a photon marker system for fiber material of the general character described which quickly and accurately ascertains authenticity, purity and provenance of yarns, threads, cloth, fabrics, finished textiles and garments is a further consideration of the present invention.

An additional consideration of the present invention is to provide a photon marker system for fiber material of the general character described comprising luminescent nano-particle photon markers within a cellulose based fiber strand.

A still further feature of the present invention is to provide a photon marker system for fiber material of the general character described which employs a spectrophotometer reader for authenticity verification.

Other aspects, features and considerations of the present invention in part will be readily apparent and in part will be pointed out hereinafter.

With these ends in view, the invention finds embodiment in various combinations of elements, arrangements of parts and series of steps by which the above-mentioned aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings in which are shown an exemplary embodiment of the invention.

DESCRIPTION OF THE PREFERRED EMBODIMENT

Figure 1A:
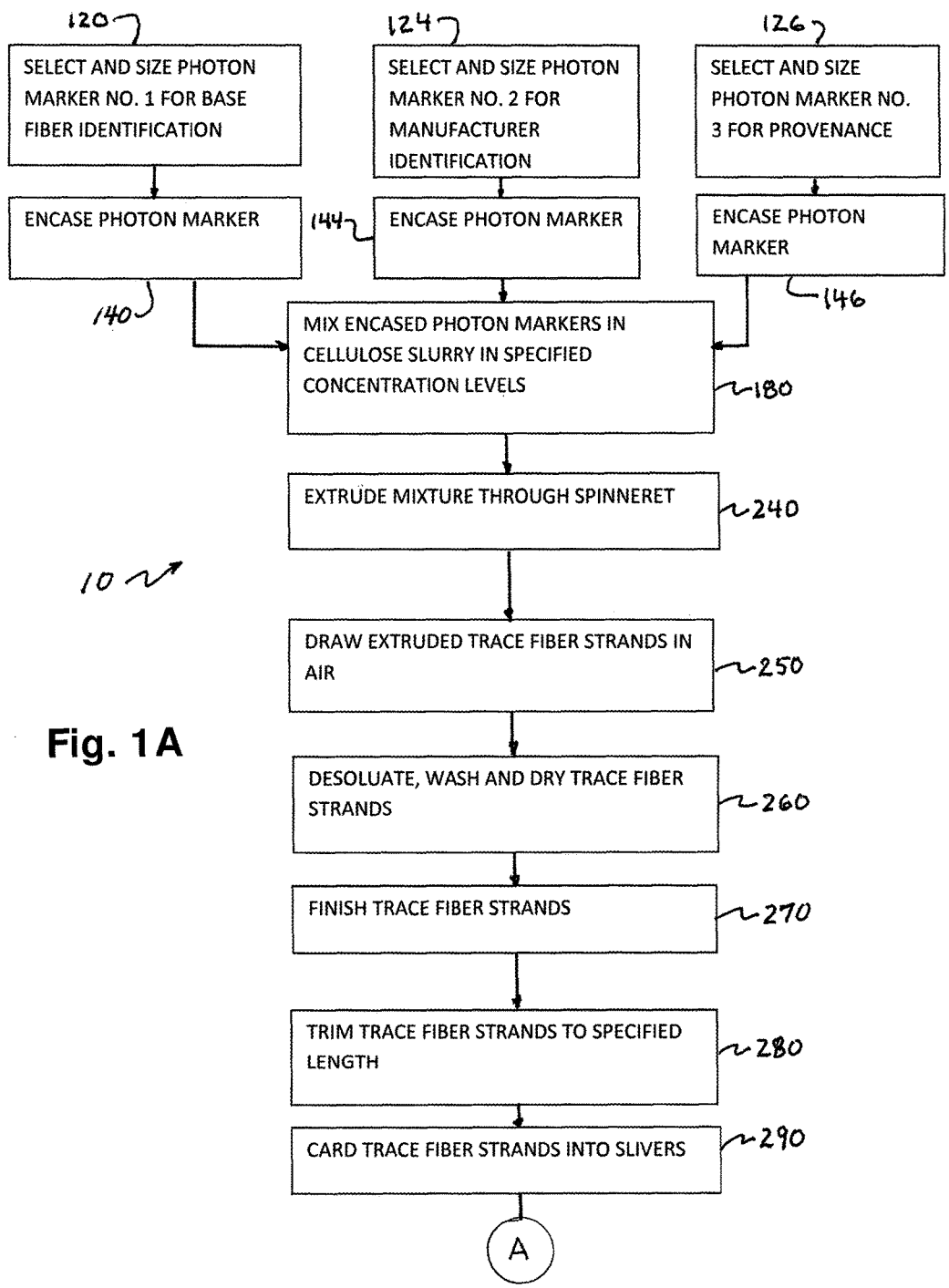
FIG. 1A is a flow chart depicting a segment of the photon marker system of the present invention.
Figure 1B:
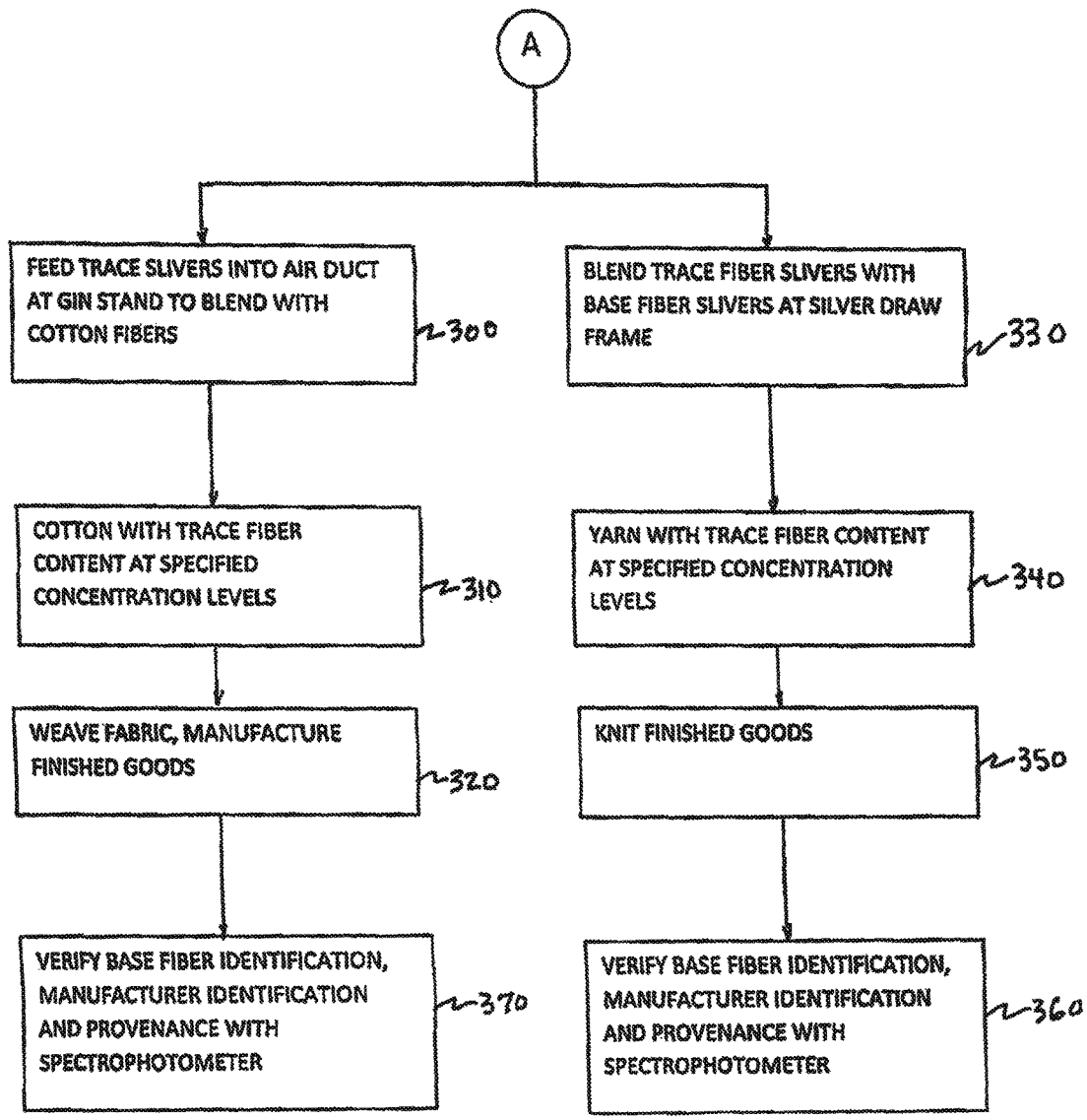
FIG. 1B is a continuation of the flow chart depicted in FIG. 1A.
Figure 2:
FIG. 2 is a schematized depiction of a photon marker in accordance with the invention and a microcapsule comprising the photon marker after encasement.

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Applicants do not intend for any term in the specification or claims to be ascribed an uncommon or special meaning unless explicitly set forth as such. Further, the present invention encompasses present and future known equivalents to the known components referred to herein by way of illustration.

The reference numeral 10 denoted generally a flow chart of the various aspects of the system of the present invention. Pursuant to the invention, luminescent nano-particle photon markers 12 e.g. photon marker No. 1, photon marker No. 2, photon marker No. 3, etc., are each processed into a core having a finished size of approximately 5 µm, as depicted in blocks 120, 124 and 126. In blocks 120, 124 and 126 signature functions have been assigned for fiber identification, manufacturer identification and provenance by way of example only.

Photon markers which may be employed include nano-particles across the visible and invisible light spectrum including UV, IR and RF and include rare earth materials, such as Lanthanides. Preferably the photon markers 12 exhibit terahertz wavelengths of between 380 nm and 100 µm.

Lanthanides exhibit strong electromagnetic and light properties because of the presence of unpaired electrons in the f-orbitals. The majority of the Lanthanides are paramagnetic, which means that they have strong magnetic fields. The basicity series which may be employed as photon markers in the present invention is made up of but not limited to the following: $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$ A further family for luminescent nano-particle photon markers include inorganic luminescent rare earth materials, wherein the emission spectrum is such that it essentially represents the fingerprint of the product to be identified. The luminescent material has preferably a mean particle size of 5 µm. It is particularly preferred that all the particles present are nearly spherical particles.

In a preferred embodiment, the luminescent material is an inorganic solid state compound which either is self-activated, i.e., exhibits donor acceptor luminescence or charge transfer luminescence (intrinsic luminescence), or is activated with one or several luminescent ions from the group of $In^+$, $Sn^{2+}$, $Pb^{2+}$, $Sb^{3+}$, $Bi^{3+}$, $Ce^{3+}$, $Ce^{4+}$, $Pr^{3+}$, $Nd^{3+}$, $Sm^{2+}$, $Sm^{3+}$, $Eu^{2+}$, $Eu^{3+}$, $Gd^{3+}$, $Tb^3$, $Dy^{3+}$, $Ho^{3+}$, $Er^{3+}$, $Tm^{2+}$, $Tm^{3+}$, $Yb^{2+}$, $Yb^{3+}$, $Ti^{3+}$, $V^{2+}$, $V^{3+}$, $V^{4+}$, $Cr^{3+}$, $Mn^{2+}$, $Mn^{4+}$, $Fe^{3+}$, $Fe^{4+}$, $Fe^{5+}$, $Co^{3+}$, $Co^{4+}$, $Ni^{2+}$, $Cu^+$, $Ru^{2+}$, $Ru^{3+}$, $Pd^{2+}$, $Ag^+$, $Ir^{3+}$, $Pt^{2+}$ and $Au^+$ (extrinsic luminescence).

The inorganic solid state compound is a binary, ternary or quaternary halogenide, oxide, oxyhalogenide, sulfide, oxysulfide, sulfate, oxysulfate, nitride, oxynitride, nitrate, oxynitrate, phosphide, phosphate, halophosphate, carbonate, silicate, halosilicate, oxysilicate, vanadate, molybdate, tungstenate, germanate or oxygermanate of the elements Li, Na, K, Pb, Mg, Ca, Sr, Se, Y, La, Ti, Zr, Hf, Nb, Ta, Zn, Gd, Lu, Al, Ga and In.

A third family comprises solid state compounds and can include any of the following: Me(S, Se) (Me=Mg, Ca, Sr, Ba, Zn, Cd), $Ln_2O_2S$ (Ln=Y, La, Gd, Lu), MgO, ZnO, $Sc_2O_3$, $Y_2O_3$, $La_2O_3$, $Gd_2O_3$, $Lu_2O_3$, $TiO_2$, $ZrO_2$, $HfO_2$, $Nb_2O_5$, $Ta_2O_5$, $Al_2O_3$, $Ga_2O_3$, $In_2O_3$, $SiO_2$, $GeO_2$, $SnO_2$, $LnBO_3$ (Ln=Sc, Y, La, Gd, Lu), $Ln(BO_2)_3$ (Ln=Sc, Y, La, Gd, Lu), $Me_3(BO_3)_2$ (Me=Mg, Ca, Sr), $MeB_4O_7$ (Me=Ca, Sr, Ba), $Me_3Ln(BO_3)_3$ (Me=Ca, Sr, Ba and Ln=Y, Gd, Lu), $LnMgB_6O_{10}$ (Ln=Y, La, Gd, Lu), $LnAl_3(BO_3)_4$ (Ln=Y, La, Gd, Lu), $MeAl_2O_4$ (Me=Mg, Ca, Sr, Ba), $MeAl_{12}O_{19}$ (Me=Ca, Sr, Ba), $Me_4Al_{14}O_{25}$ (Me=Sr, Ba), $Ln_3Me_5O_{12}$ (Ln=Y, Gd, Lu and Me=Al, Ga, Sc), $Me_3Al_2Si_3O12$ (Me=Mg, Ca), $Me_3Ln_2Ge_3O_{12}$ (Ln=Y, Gd, Lu and Me=Sr, Ba), $MeMgAl_{10}O_{17}$ (Me=Ca, Sr), $MeAlO_2$ (Me=Li, Na. K), $LiM_5O_8$ (M=Al, Ga, In), $LnMgAl_{31}O_{19}$ (Ln=La, Gd), $LnAlO_3$ (Ln=Y, La, Gd, Lu), $LnGaO_3$ (Ln=La, Gd, Lu), $LnInO_3$ (Ln=La, Gd, Lu), $Me_2TiO_4$, $MeTiO_3$ (Me=Mg, Ca, Sr, Ba) and $Ln_2Ti_2O_7$ (Ln=Y, La, Gd, Lu)

The sized photon markers 12 are encased in a shell 14 by mixing in diluted cellulose, as indicated in blocks 140, 144 and 146 to form microcapsules 16. The shell 14 serves to avoid settlement when mixed into a main batch. The shell 14 is formed in a doping process where smaller luminescent materials attach themselves to the core material; they are primarily made up of Ti and Mg ions, which are capable of storing UV excitation energy and then emitting it in the visible range over a long period of time. The shell luminescent materials combine a longer afterglow with anti-Stokes luminescence and offer unique optical emission properties for the smaller sized particles while optimizing less power level to excite the larger luminescent materials.

Figure 3:
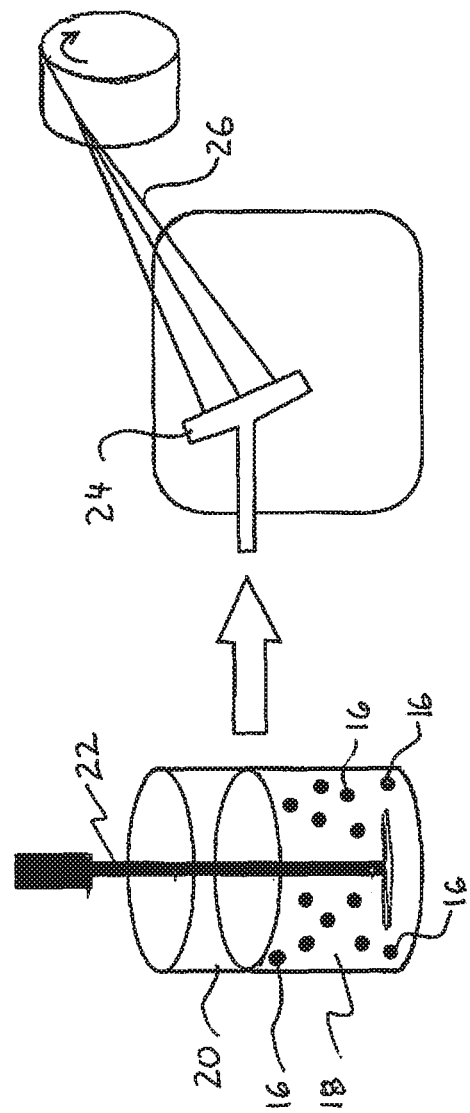
FIG. 3 is a depiction of specific concentrations of different photon marker microcapsules being mixed in cellulose slurry and then extruded through a spinneret to form trace fiber strands.

As indicated in a block 180, the microcapsules 16 are then batch mixed in cellulose slurry 18 comprising cellulose dissolved in N-Methylmorpholin-N-oxide and carried in a vessel 20 equipped with a mixer 22 (shown in FIG. 3).

A typical batch is made of a 100% formulation which is controlled by both the application and concentration levels of both microcapsules and fibers. Each batch carries a unique signature which is made up of a matrix of different percentage mix, e.g., 2, 3 or 4 different microcapsules. By controlling the different percentage mixes, each batch has its own unique frequency waveband allowing for various signatures to be produced.

The mixture of evenly distributed microcapsules and diluted cellulose is then pumped to a spinneret 24 and continuous trace fiber strands 26 are extruded through the spinneret head, as indicated in a block 240.

The trace fiber strands 26 are drawn in air, as depicted in a block 250, to align the cellulose molecules and strengthen the trace fiber strands. The trace fiber strands 26 are then immersed into a water bath, where dissolution of the cellulose sets the fiber strands; the bath contains some dilute amine oxide in a steady state concentration. Then the trace fiber strands 26 are washed with de-mineralized water. The trace fiber strands 26 next pass to a drying area, where the water is evaporated, all as indicated in a block 260

The trace fiber strands 26 then pass to a finishing area, where a lubricant, which may be soap or silicone or other agent, depending on the future use of the fiber, is applied. This step is basically a detangler, as indicated on a block 270.

The dried, finished trace fiber strands 26 are at this stage in a form called tow, a large untwisted bundle of continuous lengths of filament. The bundles of tow are taken to a cutting machine to trim to exact length, as indicated in a block 280.

Thereafter the trimmed trace fiber strands 26 are processed through a carding machine, to separate and order the strands into trace fiber slivers 28, which are coiled in a sliver can 30, as indicated in a block 290. The trace fiber slivers 28 are then blended with base fibers in specific proportions.

Figure 4:
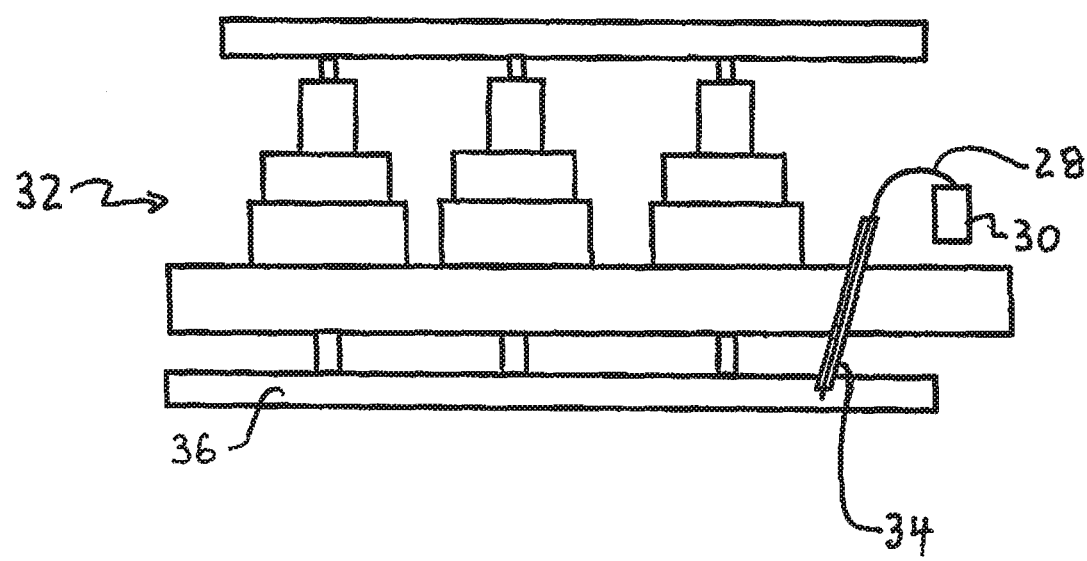
FIG. 4 is a an schematized depiction of a cotton gin stand illustrating the introduction of trace fiber slivers into an air flow duct to be blended with cotton fibers.

In instances wherein the base fiber is cotton, the trace fiber strands 28 may be blended at a cotton gin stand 32, depicted in FIG. 4. Pursuant to the invention, a delivery unit 34 feeds the trace fiber slivers 28 into an air flow duct 36 that runs beneath the gin stand 32, as indicated in a block 300. At the gin stand 32, cotton fibers (known as lint) are freed from seeds and other contaminants. The trace fiber slivers 28 are added to the cotton fibers at a specific rate based on the final application and the speed each gin is running at. The air flow duct 36 then blends all the fibers from each gin stand and feeds into a blow chamber before traveling to a baler, as indicated in a block 310. This process allows for homogenous distribution of trace fiber slivers 28 through each bale. The cotton is then employed to weave fabric and the manufacture of finished textile products, as indicated in a block 320.

Figure 5:
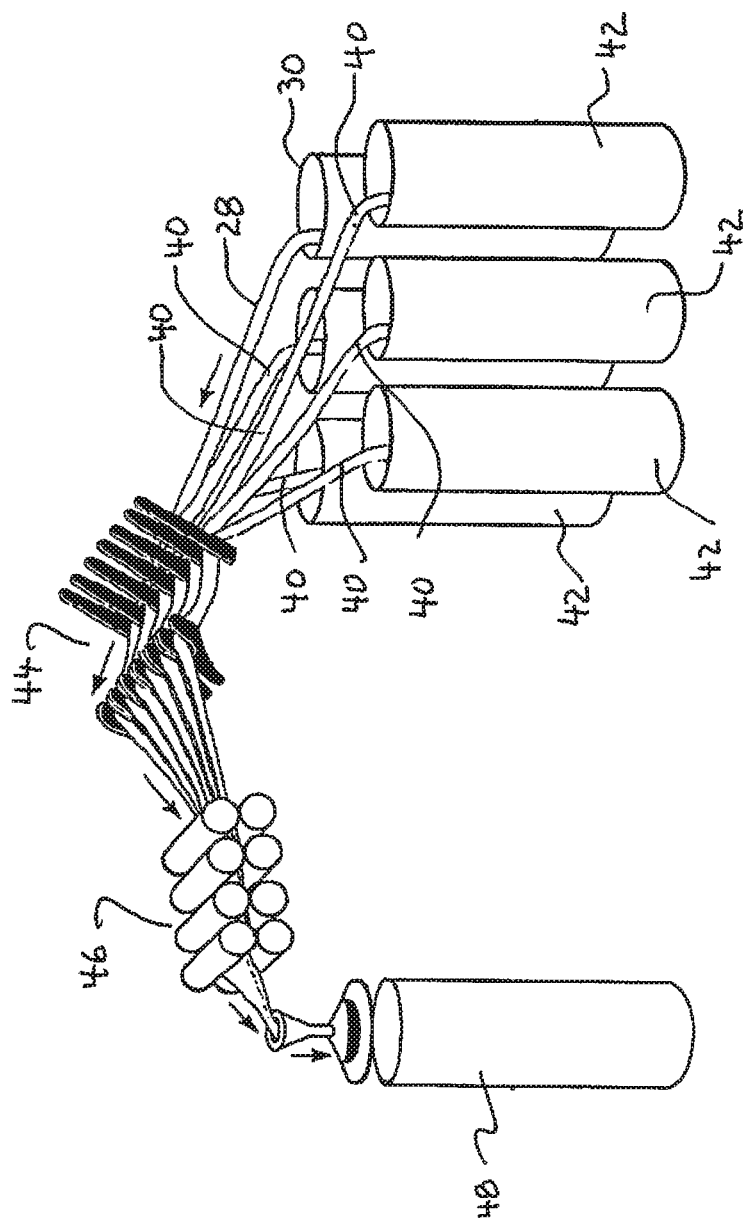
FIG. 5 is a depiction of a sliver draw frame for blending trace fiber slivers with cotton slivers and FIG. 6 is a depiction of a garment manufactured with fabric having trace fiber slivers in accordance with the invention and a spectrophotometer reader accessing the photon marker microcapsules of the trace fiber slivers for reading one or more characteristics for authenticity verification.

If yarn is to be produced, the trace fiber slivers 28 are blended with cotton fiber at a sliver draw frame 38, in a standard spinning process depicted in FIG. 5. At the sliver draw frame 38, the trace fiber slivers 28, coiled in the sliver can 30, are blended with cotton slivers 40, coiled in cotton sliver cans 42. Specific concentrations of trace fiber slivers 28 and cotton fiber slivers 40 are employed, as determined by the end application. The slivers 28, 40 pass through a spoon comb 44 and then through a series of rollers 46. The slivers 28, 40 are then twisted into yarn and coiled in a yarn can 48 as depicted in a block 330. The yarn with trace fiber slivers is then employed to knit finished textile products, as indicated the blocks 340 and 350.

Figure 6:
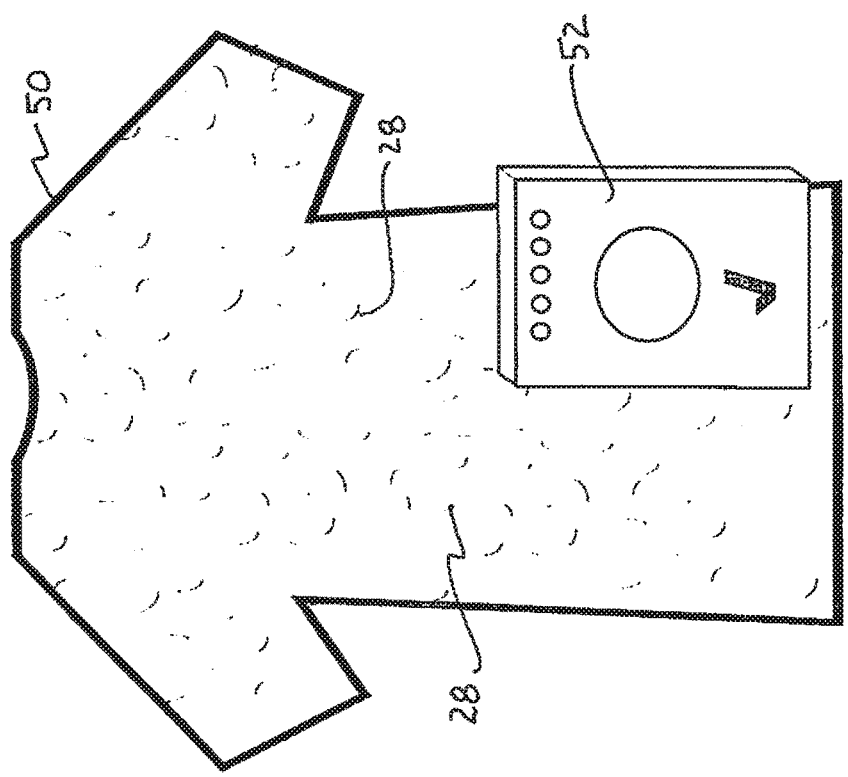

Illustrated in FIG. 6 a garment 50 manufactured with fabric having trace fiber slivers 28 in accordance with the invention. Also illustrated is a spectrophotometer reader 52 accessing the photon marker microcapsules of the trace fiber slivers and reading one or more characteristics for authenticity verification. The trace fiber slivers are invisible to the naked eye and are depicted as visible in FIG. 6 for the purpose of illustration only.

The reader 52 is uniquely programmed to detect the precise signatures of each batch frequency waveband. For example, the reader 52 emits a signal at a predetermined waveband which is linked only to the specific photon markers carried in the trace fiber slivers. The reader receives back a specific waveband signal to confirm their presence. The reader can be programmed to detect preset signatures for, among other parameters: 1) proof of provenance—identification; 2) verification—proof of provenance and brand owner; 3) authentication—minimum specified base fiber content; 4) quantification—unauthorized adulteration of fiber content; and 5) the assigned model or style number.

The reader 52 is programmed to record and date stamp all information retrieved along with the GPS tracked location of the reading. Recorded data is uploaded into the cloud for transparency throughout the supply chain.

It should be understood that while the exemplary embodiment illustrated the base fiber material as being cotton, the invention is equally applicable to other natural base fibers such as wool, cashmere, alpaca, linen, silk, flax, hemp, mohair, jute, ramie, sisal, catgut, etc. Similarly, the trace fiber slivers can be blended with man-made base fibers, e.g., cellulose, viscose-rayon, modal, etc., as well as synthetic base fibers such as nylon, acrylic, silicon carbide, and polyethylene terephthalate. The trace fiber slivers 28 are blended with the natural, man-made and synthetic base fibers at a sliver draw frame as described with respect to the cotton fiber slivers.

Thus is will be seen that there is provided a photon marker system for fiber material which achieves the various aspects, features and considerations of the present invention and which is well suited to meet the conditions of practical usage.

As various possible further embodiments might be made of the present invention and various changes might be made in the illustrative embodiment above set forth without departing from the spirit of the invention, it is to be understood that all matter herein described or shown in the accompanying drawings is to be interpreted as illustrative and not in a limiting sense.

Having thus described the invention, there is claimed as new and desired to be secured by Letters Patent:

1. A yarn or thread comprising a base fiber uniformly blended with trace fiber slivers, said trace fiber slivers comprising luminescent nano-particle photon marker microcapsules evenly distributed within cellulose fibers, the luminescent nano-particle photon marker microcapsules transmitting a reflected response signature within a wavelength range of 380 nm and 100 µm when examined under a spectrophotometer reader, the response signature being indicative of an aspect of the yarn, thread or any intermediate or final product manufactured therefrom.

2. The yarn or thread constructed in accordance with claim 1 further including a plurality of different luminescent nano-particle photon marker microcapsules, each comprising a different rare earth material and having a different response signature indicative of a different aspect of the yarn, thread or any intermediate or final product manufactured therefrom, the different response signatures being a function of the concentration level of each different luminescent nano-particle photon marker microcapsule.

3. The yarn or thread constructed in accordance with claim 1 wherein the luminescent nano-particle photon marker microcapsules comprise a core of substantially spherical rare earth ceramic material approximately 5 μm in diameter.

4. The yarn or thread constructed in accordance with claim 3 wherein the core of substantially spherical rare earth ceramic material is encased in a shell.

5. The yarn or thread constructed in accordance with claim 1 wherein the luminescent nano-particle photon marker microcapsules comprise a core of rare earth ceramic material selected from the group consisting of $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$ and $Lu^{3+}$.

6. The yarn or thread constructed in accordance with claim 1 wherein the luminescent nano-particle photon marker microcapsules comprises an inorganic solid state compound which is self-activated.

7. The yarn or thread constructed in accordance with claim 1 wherein the luminescent nano-particle photon marker microcapsules comprises an inorganic solid state compound which exhibits donor acceptor luminescence or charge transfer luminescence.

8. A garment manufactured of yarn or thread constructed in accordance with claim 1.

9. A method of verifying the authenticity of a garment constructed in accordance with claim 8, the method comprising the steps of:
  a) providing a spectrophotometer reader programmed to respond to radiant energy emissions corresponding to the wavelength of the response signature of the luminescent nano-particle photon marker microcapsules,
  b) actuating the spectrophotometer reader to emit radiant energy triggering the response signature,
  c) capturing the response signature emitted by the luminescent nano-particle photon marker microcapsules, and
  d) verifying whether the captured response signature corresponds to that of the luminescent nano-particle photon marker microcapsules.

10. The yarn or thread constructed in accordance with claim 1 wherein the base fiber is selected from the group consisting of natural fibers, man-made fibers and synthetic fibers.

11. A method of verifying the authenticity of yarn or thread constructed in accordance with claim 1, the method comprising the steps of:
  a) providing a spectrophotometer reader programmed to respond to radiant energy emissions corresponding to the wavelength of the response signature of the luminescent nano-particle photon marker microcapsules,
  b) actuating the spectrophotometer reader to emit radiant energy triggering the response signature,
  c) capturing the response signature emitted by the luminescent nano-particle photon marker microcapsules, and
  d) determining whether the base fiber has been adulterated by comparing the captured response signature strength to the response signal strength of undiluted base fiber.

12. A method of identifying a yarn, thread or any intermediate or final product manufactured therefrom, the method comprising the steps of:
  a) uniformly blending in the yarn or thread trace fiber slivers comprising cellulose fibers having evenly distributed luminescent nano-particle photon markers, the nano-particle photon markers having a predetermined response signature wavelength;
  b) capturing a response signature emitted by the luminescent nano-particle photon markers; and
  c) comparing the captured response signal to the predetermined response signature wavelength.

13. The method of identifying a yarn, thread or any intermediate or final product manufactured therefrom in accordance with claim 12 wherein step a) includes distributing a plurality of different luminescent nano-particle photon markers, each having a predetermined response signature wavelength, step b) includes capturing a response signature emitted by each different luminescent nano-particle photon marker and step c) includes comparing each captured response signal to one of the predetermined response signature wavelengths.

14. The method of identifying a yarn, thread or any intermediate or final product manufactured therefrom in accordance with claim 13 wherein step b) and step c) are performed at different stages of production of the intermediate or final product.

15. A photon marker system for verification of the authenticity of a garment which has been woven or knitted from one or more base fibers, the system comprising a plurality of trace fiber slivers blended within yarn or thread from which the garment has been woven or knitted, the trace fiber slivers comprising photon markers having a predetermined response signature wavelength the system further including a spectrophotometer reader for determining whether the yarn or thread generates a response signal corresponding to the predetermined response signature wavelength.

16. The photon marker system for verification of the authenticity of a garment in accordance with claim 15 further including a plurality of different luminescent nano-particle photon markers within the trace fiber slivers, each luminescent nano-particle photon marker having a predetermined response signature wavelength, wherein the spectrophotometer reader determines a plurality of different authenticity aspects, each corresponding to one of the predetermined response signature wavelengths.

* * * * *